(12) United States Patent
Van Dorpe et al.

(10) Patent No.: US 9,146,235 B2
(45) Date of Patent: Sep. 29, 2015

(54) INTEGRATED FLUORESCENCE DETECTION

(71) Applicants: IMEC VZW, Leuven (BE); Katholieke Universiteit Leuven, KU LEUVEN R&D, Leuven (BE)

(72) Inventors: Pol Van Dorpe, Spalbeek (BE); Sarp Kerman, Leuven (BE); Peter Peumans, Herfelingen (BE); Willem Van Roy, Bierbeek (BE)

(73) Assignees: IMEC VZW, Leuven (BE); Katholicke Universiteit Leuven, KU LEUVEN R&D, Leuven (BE)

( * ) Notice: Subject to any disclaimer, the term of this patent is extended or adjusted under 35 U.S.C. 154(b) by 0 days.

(21) Appl. No.: 14/570,675

(22) Filed: Dec. 15, 2014

(65) Prior Publication Data
US 2015/0168392 A1    Jun. 18, 2015

(30) Foreign Application Priority Data

Dec. 14, 2013    (EP) .................................... 13197307

(51) Int. Cl.
| G01N 21/64 | (2006.01) |
| G01N 21/77 | (2006.01) |
| G01N 33/50 | (2006.01) |
| G01N 33/543 | (2006.01) |

(52) U.S. Cl.
CPC ........ G01N 33/54373 (2013.01); G01N 21/648 (2013.01); G01N 21/6428 (2013.01); G01N 21/6454 (2013.01); G01N 21/7743 (2013.01); G01N 2021/6482 (2013.01)

(58) Field of Classification Search
CPC ................. G01N 2021/6482; G01N 21/6428; G01N 21/6454; G01N 21/648; G01N 21/7743; G01N 33/54373
See application file for complete search history.

(56) References Cited

U.S. PATENT DOCUMENTS

| 2004/0222480 A1* | 11/2004 | Weisbuch et al. ............. 257/433 |
| 2008/0278722 A1* | 11/2008 | Cunningham et al. ........ 356/317 |
| 2010/0320363 A1 | 12/2010 | Schleipen |
| 2011/0031409 A1* | 2/2011 | Cunningham et al. ..... 250/458.1 |

FOREIGN PATENT DOCUMENTS

| EP | 1085315 A1 | 3/2001 |
| EP | 1972909 A1 | 9/2008 |

OTHER PUBLICATIONS

European Search Report, European Patent Application No. 13197307.5, dated May 21, 2014.
Grandin, H.M. et al., "Waveguide Excitation Fluorescence Microscopy: A New Tool for Sensing and Imaging the Biointerface", Biosensors and Bioelectronics, vol. 21, No. 8, Feb. 15, 2006, pp. 1476-1482.

* cited by examiner

*Primary Examiner* — Mark R Gaworecki
(74) *Attorney, Agent, or Firm* — McDonnell Boehnen Hulbert & Berghoff LLP (57) ABSTRACT

An integrated fluorescence detector for detecting fluorescent particles is described. An example integrated fluorescence detector comprises a substrate, the substrate comprising an integrated detection element for detecting fluorescence radiation from fluorescent particles upon excitation of the particles with incident excitation radiation. The integrated fluorescence detector also comprises a sensing layer adapted for accommodating fluorescent particles to be sensed. The integrated fluorescence detector further comprises a photonics crystal layer arranged in between the sensing layer and the substrate, the photonics crystal layer comprising an absorption material designed such that the photonics crystal layer is configured for diffracting incident excitation radiation into a lateral direction in which the photonics crystal layer extends for incident excitation radiation having a wavelength within at least 10 nm of the predetermined excitation wavelength.

13 Claims, 6 Drawing Sheets

INTEGRATED FLUORESCENCE DETECTION

CROSS-REFERENCE TO RELATED APPLICATION

Priority is claimed to European Patent Application No. 13197307.5 filed Dec. 14, 2013, the contents of which are hereby incorporate by reference.

FIELD OF THE INVENTION

The invention relates to the field of sensing. More particularly, the present invention relates to methods and systems for detecting fluorescence using an integrated fluorescence detector and for limiting a disturbance effect of the excitation source in the detector.

BACKGROUND OF THE INVENTION

Fluorescence is a wide-spread technique in biology to investigate several problems, ranging from cellular and in vivo imaging to molecular diagnostics. The technique is based on labelling particles of interest with fluorophores and on detecting the labelled particles by irradiating them with an excitation source and detecting the fluorescent emission. In molecular diagnostics, fluorescence is often used to determine the concentration of an analyte, i.e., the particles of interest. Although this is a very sensitive technique, it usually requires expensive and bulky free-space optics.

Several efforts have been made to miniaturize fluorescence detection setups. Miniaturisation has been obtained by integrating the detector into the sensing element. Fluorescence is generated by optical excitation of fluorescent particles that typically are immobilized on the surface of the sensing element. The subsequent emission of fluorescence by these particles is then detected by a detector integrated in the sensing element. In order to efficiently excite the fluorescent particles, this involves typically a strong radiation source (usually a laser source), that has a shorter wavelength than the wavelength of the fluorescence emission. The optical power in the excitation source is orders of magnitude larger than the emission from the molecules. Therefore, the excitation wavelength has to be strongly rejected, in order not to obscure the emitted radiation or even in order not to prevent detection from being possible, e.g. through saturation of the detector.

In existing, free-space, fluorescence setups, this is accomplished by making use of free-space optical elements such as a dichroic mirror and interference filters. Such elements are readily available and have proven efficiency. Nevertheless, when the detector is integrated in the sensing element, such filters need to be integrated in the device. For an integrated solution, such a filter needs to be introduced between the sensor surface, where the fluorescence particles are immobilized and excited, and the detector where the fluorescence detection needs to be detected. For very low emission detection, e.g., for the detection of very low concentrations, the rejection has to be very strong. Rejection ratios of 6 to 8 orders of magnitude, thus corresponding with optical density OD6-OD8, may be required, which sets very large constraints on the excitation radiation filter.

Some solutions have already been investigated. In one solution, interference filters were used as rejection filter for rejecting excitation radiation from the detector. Nevertheless, for reaching rejection ratios in the order of OD6 to OD8 rejection, the amount of layers in the interference filter need to be high and the thicknesses of the layers to be used is very small. Manufacturing of such interference filters is typically e complex and/or time consuming.

Another solution is the use of absorption based filters. Nevertheless, such filters typically suffer from heat generation in the filter, which may result in deterioration of the rejection properties as well as on the overall sensing quality of the sensor. Furthermore, it may be difficult to find an appropriate absorption material that absorbs at the proper excitation wavelength and that is transparent for the emission of the fluorescence particles of the most commonly used dyes.

SUMMARY OF THE INVENTION

It is an object of embodiments of the present invention to provide methods and systems for integrated fluorescence detection that combine miniaturization with high sensitivity for fluorescence detection whilst being less prone to environmental and process variations.

It is an advantage of embodiments of the present invention that methods and systems are provided for integrated fluorescence detection that allows easier matching between the wavelength for which the fluorescence detection device/method is optimised and the wavelength of the excitation beam to be used for proper operation.

It is an advantage of embodiments of the present invention that the impact of wavelength shifts of the excitation wavelength for which the detection device/method is optimised, caused by environmental and/or process variations, can be reduced, resulting in fluorescence detection systems still having a good sensitivity.

It is an advantage of embodiments of the present invention that the specifications on the rejection integrated filter for rejecting the excitation radiation from the detector can be relaxed. It is an advantage of embodiments of the present invention that not only good rejection (filtering) of the excitation radiation from the detector can occur by the filter, but that also, using the same power of the excitation source, more efficient excitation of the fluorescence particles is reached, as the filter also effects the excitation efficiency. It is an advantage of embodiments of the present invention that, at the sensing surface where the fluorescence particles are mobilized, an effective enhancement of the optical field can be obtained. These advantages are substantially maintained, even if the excitation wavelength for which the device is optimised is slightly shifted due to environmental and/or process variations.

It is an advantage of embodiments of the present invention that as a result of the above, a lower excitation power can be used for reaching a similar fluorescence detection sensitivity.

It is an advantage of embodiments according to the present invention that nano-photonic elements can be used for high excitation efficiencies of fluorescence particles, with homogeneous excitation efficiencies i.e., a constant optical intensity at the sensor surface, whereby the effect of environmental and/or process variations on the efficiency that can be reached by the fluorescence detector can be reduced or limited. It is an advantage of embodiments according to the present invention that the high efficiency reached by the detector can be based on redirection of the excitation radiation for avoiding that it enters the detector. It is an advantage of embodiments according to the present invention that the rejection filter can be easily integrated in the device, using conventional processing techniques.

The present invention relates to an integrated fluorescence detector for detecting fluorescent particles, the integrated fluorescence detector comprising a substrate, the substrate comprising an integrated detection element for detecting fluorescence radiation from fluorescent particles upon excitation of the particles with incident excitation radiation, a sensing layer adapted for accommodating fluorescent particles to be sensed, wherein the detector furthermore comprises a photonics crystal layer arranged in between the sensing layer and the substrate, the photonics crystal layer being designed for diffracting the incident excitation radiation with the predetermined excitation wavelength into a lateral direction in which the photonics crystal layer extends, the photonics crystal layer comprising an absorption material such that the photonics crystal layer is configured for diffracting incident excitation radiation into a lateral direction in which the photonics crystal layer extends for excitation radiation having a wavelength in a wavelength range spanning at least 10 nm around the predetermined excitation wavelength.

It is an advantage of embodiments according to the present invention that an accurate rejection filter is obtained for rejecting excitation radiation from a detector positioned under a fluorescence sensing layer where fluorescent particles can be bound.

The photonics crystal layer may comprise an absorption material having an extinction coefficient k (being the imaginary part of the refractive index) in a range between 0.03 and 0.3 in the wavelength range where the fluorescent dye absorbs, while having an extinction coefficient k below 0.03 in the wavelength region where the dye emits.

The photonics crystal layer may be arranged with respect to the sensing layer such that, upon propagation of the diffracted incident excitation radiation into the lateral direction, the propagation mode of the diffracted excitation radiation has an evanescent tail in the sensing layer, thus allowing further excitation of fluorescent particles accommodated at the sensing layer. It is an advantage according to embodiments of the present invention that the rejected radiation is guided such that it provides further excitation possibilities for exciting the accommodated fluorescent particles. In this way the required excitation power generated at the source can be reduced. It is an advantage of embodiments according to the present invention that fluorescent particles not bound to the surface, e.g. in the fluid sample above the substrate, are not additionally excited by the propagating excitation radiation in lateral direction, thus no additional parasitic fluorescence is induced.

The photonics crystal layer may comprise a waveguide and a grating. It is an advantage of embodiments according to the present invention that the grating can be designed so as to enhance fluorescence excitation in a robust way, i.e. substantially insensitive to process and environmental variations.

The grating may be a one dimensional varying structure.

The photonics crystal layer may comprise a grating with a two dimensional varying structure. It is an advantage of embodiments according to the presence invention that the two dimensional surface structuring may be arranged so as to reduce polarization effects of the incident radiation.

The sensing layer may be functionalized for binding the fluorescent particles. It is an advantage of embodiments according to the present invention that analysis can be performed with high specificity.

The photonics crystal layer may be made of a CMOS (complimentary metal-oxide semiconductor) processable material. It is an advantage of embodiments according to the present invention that the additional elements to be processed in the fluorescence detector can be made using similar processing steps and based on the same manufacturing platform, resulting in no significant increase of complexity for manufacturing.

The photonics crystal material may comprise an absorption material for allowing diffracting excitation radiation in a wavelength range spanning at least 10 nm.

The detector furthermore may comprise a microfluidic channel arranged for running over the sensing layer and for allowing a sample to be characterized to interact with the sensing layer.

The integrated detector may be an integrated optical detector embedded in the substrate.

The present invention also relates to a system comprising an integrated fluorescence detector as described above.

The system furthermore may comprise an excitation source for generating excitation radiation for exciting the fluorescent particles bound to the surface.

The present invention furthermore relates to a method for detecting fluorescence radiation from fluorescent particles, the method comprising providing an interaction between a sample comprising fluorescent particles and a sensing layer, providing an excitation radiation beam for exciting fluorescent particles accommodated on the sensing layer, and guiding excitation radiation away from a detection element by diffracting the excitation radiation in a lateral direction using a photonics crystal, the photonics crystal comprising absorption material such and being designed such that the photonics crystal layer is configured for diffracting incident excitation radiation into a lateral direction in which the photonics crystal layer extends for incident excitation radiation having a wavelength in a wavelength range spanning at least 10 nm around the predetermined excitation wavelength. The present invention also relates to the use of a detector as described above for detecting fluorescent particles in a sample.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments according to the present invention reference is made to lateral direction, reference is made to the direction substantially parallel to the substrate, the photonics crystal layer or the sensing layer. This direction typically will be angled, e.g. perpendicular, to the direction of the incident excitation beam. As will be demonstrated, the fact that the excitation radiation is diffracted in the lateral direction, results in it being substantially guided away from the detection element, thus resulting in less background radiation (as one typically is interested in the fluorescence signal and not in the excitation radiation).

Where in embodiments according to the present invention reference is made to radiation being diffracted, e.g. in a lateral direction, this means that advantageously as much as possible of the radiation in the beam is diffracted. If reference is made to a beam being diffracted, redirected, transmitted or absorbed, typically at least 50% of the beam, advantageously at least 75% of the beam is diffracted, redirected, transmitted or absorbed. Where in embodiments according to the present invention reference is made to a photonics crystal layer, reference is made to a layer forming or being part of a photonics crystal. Photonic crystals are periodic optical nanostructures that affect the motion of photons. The periodic structures thus formed may have a one dimensional structural variation, i.e. whereby the variation in structure occurs substantially only in one direction, or may be a two dimensional structural variation whereby the variation in structure typically occurs also in a second direction not coinciding with the first direction.

Where in embodiments according to the present invention reference is made to absorption material, reference is made to a material having an extinction coefficient k in a range between 0.03 and 0.3 in the wavelength range where the fluorescent dye absorbs, while the extinction coefficient is below 0.03 in the wavelength region where the dye emits. Such materials are referred to as high loss materials.

In a first aspect, the present invention relates to an integrated fluorescence detector. Such a detector is used for detecting fluorescence, e.g., for detecting fluorescent particles in a sample. Often fluorescent particles, also referred to as fluorophores or dyes, are used to bind to particular target particles of interest, in order to detect or quantify the particles of interest through the fluorescent particles attached thereto. The detector envisaged is an integrated detector, meaning that the detection element is integrated, either homogeneously, heterogeneously or a combination thereof. According to embodiments, the fluorescence detector is optimized for fluorescence detection using a predetermined excitation wavelength. The fluorescence detector comprises a substrate comprising an integrated detection element. Such an integrated detection element typically may be a radiation detector for detecting fluorescence radiation from fluorescent particles upon excitation of these particles with incident excitation radiation. The detector furthermore comprises a sensing layer adapted for accommodating fluorescent particles to be sensed. Further, the detector also comprises a photonics crystal layer arranged in between the sensing layer and the substrate. The photonics crystal layer is thereby designed for diffracting the incident excitation radiation with the predetermined excitation wavelength into a lateral direction in which the photonics crystal layer extends. Nevertheless, due to environmental or process variations, the photonics crystal layer may in practice be optimal for radiation having a wavelength different from the predetermined excitation wavelength. In other words, the design may differ from the real configuration due to environmental or process variations. According to embodiments of the present invention, the photonics crystal layer therefore comprises an absorption material such that the photonics crystal layer in practice is configured for diffracting incident excitation radiation into a lateral direction in which the photonics crystal layer extends, for excitation radiation having a wavelength in a wavelength range spanning at least 10 nm around the predetermined excitation wavelength.

By way of illustration, embodiments of the present invention not being limited thereto, standard and optional components of the detector will now be discussed in more detail with reference to the drawings FIG. 2 to FIG. 3.

Figure 2:
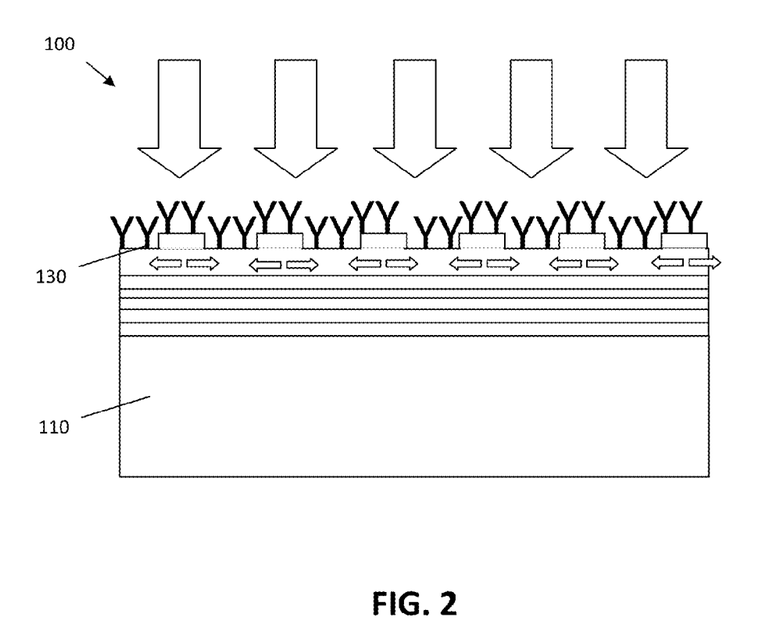
FIG. 2 illustrates a schematic view of part of an integrated sensor according to an embodiment of the present invention.

The detector 100 as shown in FIG. 2 comprises a substrate 110. The substrate may be any suitable type of substrate, which is sufficiently transparent so that the fluorescence radiation to be measured can travel therein. The actual material selection thus may be dependent on the application provided (and the fluorophores or dyes used). The "substrate" may include a semiconductor substrate such as e.g. silicon, a gallium arsenide (GaAs), a gallium arsenide phosphide (GaAsP), an indium phosphide (InP), a germanium (Ge), or a silicon germanium (SiGe) substrate. The "substrate" may include for example an insulating layer such as a $SiO_2$ or a $Si_3N_4$ layer in addition to a semiconductor substrate portion. Thus, the term substrate also includes silicon-on-glass, silicon-on sapphire substrates. Also, the "substrate" may be any other base on which the other layers can be formed and wherein the detector can be integrated somehow, for example a glass, quartz, fused silica, etc.

Figure 3:
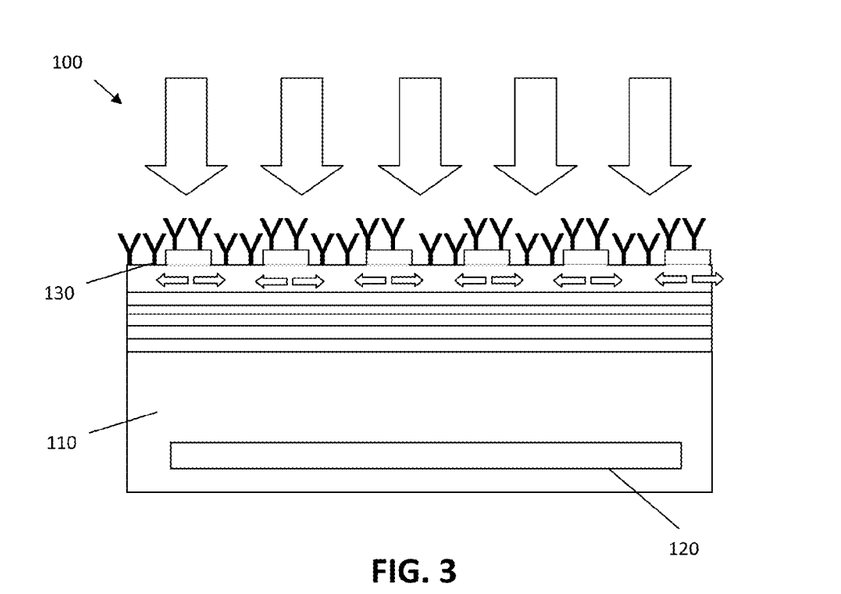
FIG. 3 illustrates a schematic view of an integrated sensor with detection element according to an embodiment of the present invention.

The substrate 100 typically also comprises a detection element 112 integrated therein, as not shown in FIG. 2 but shown in FIG. 3. The detection element 112 may be integrated in a heterogeneous manner, a homogeneous manner or a combination thereof. In some embodiments, the detection element can be formed into the substrate using CMOS compatible processing steps, which results in an efficient manufacturing process. The detection element used may be any suitable detection element allowing detection of fluorescence radiation, typically induced by excitation radiation impinging on fluorescence particles.

The detector 100 furthermore comprises a sensing layer 130. The sensing layer 130 typically is adapted for accommodating fluorescent particles. The sensing layer may be functionalized for binding fluorescent particles or the targets of interest to which the fluorescent particles are connected. The surface of the sensor device may be modified by a coating which is designed to attract certain molecules or may be modified by attaching molecules to it, which are suitable to bind the target molecules which are present in the sample fluid. Such molecules are known to the skilled person and include complementary DNA, antibodies, antisense RNA, etc. Such molecules may be attached to the surface by means of spacer or linker molecules. The surface of the sensor device can also be provided with molecules in the form of organisms (e.g. viruses or cells) or fractions of organisms (e.g. tissue fractions, cell fractions, membranes). The surface of biological binding can be in direct contact with the sensor chip, but there can also be a gap between the binding surface and the sensor chip.

The detector 100 also optionally comprises a microfluidic channel that runs over the sensing surface and by providing a sample in the channel, the sample may be brought into contact with the sensing surface. The binding surface can be under an angle with respect to, e.g. perpendicular to, the surface of the sensor chip.

The detector 100 comprises a photonic crystal layer 120 that allows guiding excitation radiation that would enter the substrate away from the detection element 112. More particularly, the photonics crystal layer 120 is arranged in between the sensing layer 130 and the substrate 110 and is configured for diffracting incident excitation radiation into a lateral direction in which the photonics crystal layer 120 extends. It may be seen as a combination of a grating with a waveguide. The photonics crystal layer may be made of any suitable material. The photonic crystal layer 120 can comprise a one-dimensional variation in structure or a two-dimensional variation in structure. Thus the nanostructured surface which corresponds with the photonics crystal layer can have a two-dimensional or one-dimensional surface structuring and can be referred to as a photonic crystal. The one-dimensional case is often also referred to as a grating.

It is known from the state of the art to provide such photonic crystal layers designed for diffracting incident excitation radiation into a lateral direction in which the photonics crystal layer 120 extends. For a given excitation wavelength, the photonic crystal layer, being a waveguide combined with a grating, can be designed such that the excitation wavelength that is coupled in laterally matches the excitation wavelength required for the fluorescence measurement. Such a design can be performed based on optical simulations based on for example (but not limited to) finite difference time domain simulations, finite element simulations, rigorous coupled wave analysis, Eigenmode expansion methods, etc. Simulations of the photonic crystal, i.e., of the grating features and the waveguide, typically may take into account the height of the grating features, the grating period, the duty cycle, the sidewall angle of the waveguide of the photonics crystal layer, the refractive index of the surrounding medium, the thickness and refractive index of the layers underneath the grating, and the like. In some embodiments also other parameters may be taken into account. As will be shown in FIG. 7, for photonic crystal layers used in the state of the art, the optimization typically results in a narrow resonance, i.e., a narrow wavelength range for which the excitation radiation is coupled in a lateral direction in the photonic crystal layer, where it can efficiently excite fluorescent particles through an evanescent tail of the excitation radiation propagating in the photonic crystal layers. Nevertheless, due to environmental and process variations the excitation wavelength for which the structure is optimized may shift and, in view of the small resonance wavelength range, not match the actual excitation wavelength anymore. In other words, due to environmental or process variations the design may differ from the real configuration. Embodiments of the present advantageously tackle this problem.

According to embodiments of the present invention, the photonics crystal layer 120 comprises an absorption material. The latter has the effect that the wavelength range of the excitation radiation for which the coupling in lateral direction in the photonic crystal layer 120 is optimized, i.e. can occur, broadens. Consequently, even if due to environmental or process variations the excitation wavelength range for which the structure is optimized slightly shifts, the excitation wavelength of the excitation radiation effectively used in order to excite the fluorescence particles will still fall within the range of optimization and the advantageous effect of having a good sensitivity for detection still will occur. Surprisingly, it was also found that the absorption material, although absorbing part of the fluorescent radiation, still allowed sufficient fluorescent radiation to reach the detector so that the relative gain in sensitivity due to the reduction in excitation radiation reaching the detector is significantly more important than the loss of intensity of fluorescent radiation. According to embodiments of the present invention, the photonics crystal layer 120 at least comprises absorption material but also may consist of absorption material, such as for example amorphous silicon, amorf Si doped with Carbon (to tune the bandgap), GaN, InGaN, AlGaAs, polymers having absorption bands in the visible part of the spectrum. Advantageously, the absorption layer has an absorption spectrum that is adapted for significantly absorbing the excitation wavelength and not (or less of) the fluorescence radiation. Advantageously the absorption material has an extinction coefficient in the range of 0.03 and 0.3 in the region where the fluorescent dye absorbs, while having an extinction coefficient below 0.03 in the wavelength region where the dye emits. The photonics crystal layer 120 may be made of a typical photonics crystal material, such as for example low-index contrast waveguide platforms (e.g. polymer waveguides, glass/silica waveguides, $Al_xGa_{1-x}As$ waveguides, $In_xGa_{1-x}As_yP_{1-y}$ waveguides), high-index contrast waveguides (e.g. Silicon-on-Insulator, semiconductor membranes), plasmonic waveguides (e.g. metal nano-particle arrays, metal layers), also called Photonic Lightwave circuits (PLC). According to particular embodiments, the sensing systems could be implemented in a silicon-on-insulator platform. The high refractive index contrast allows photonic waveguides and waveguide components with submicron dimensions to guide, bend and control light on a very small scale so that various functions can be integrated on a chip.

Figure 1:
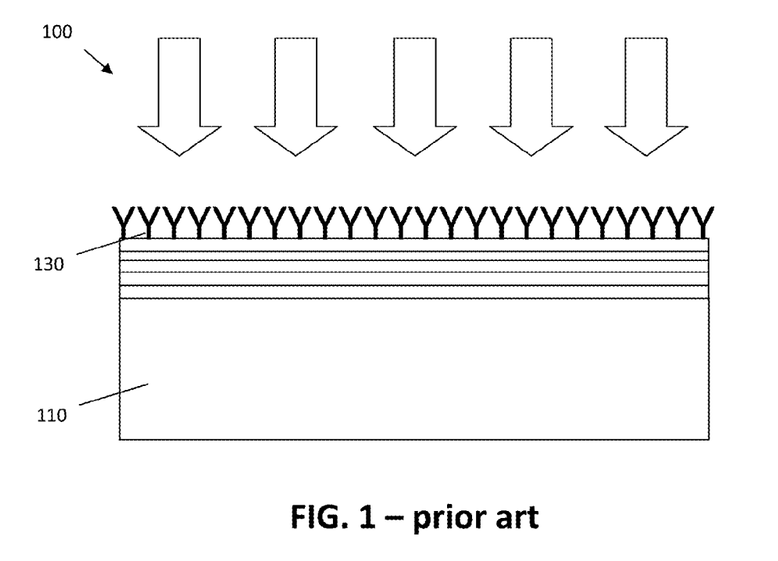
FIG. 1 provides a schematic view of part of an integrated sensor using a rejection filter as known in prior art.
Figure 4:
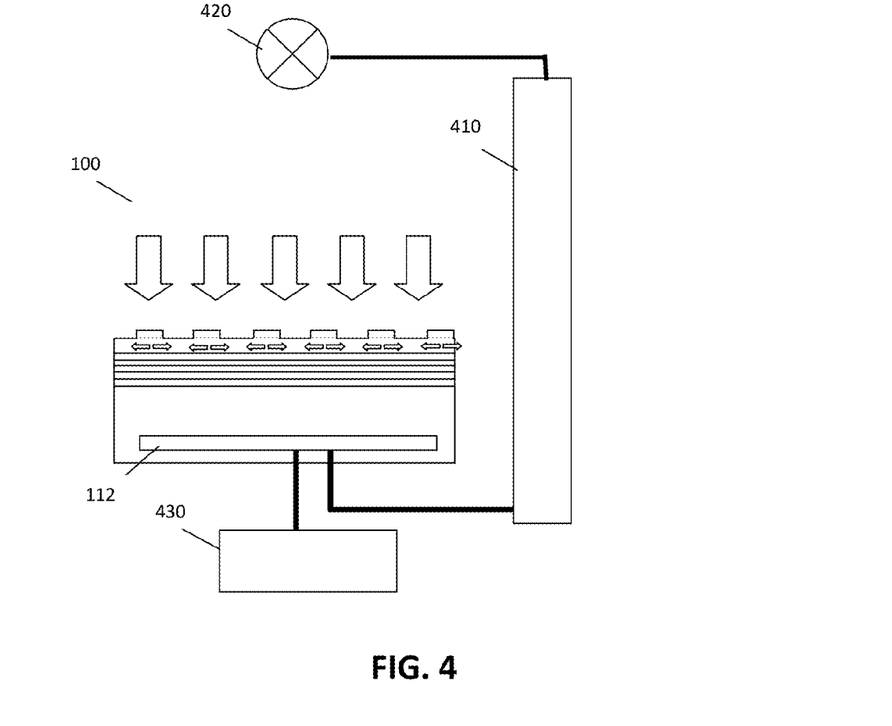
FIG. 4 illustrates a schematic representation of a detection system according to an embodiment of the present invention.

The photonics crystal layer 120 is schematically indicated in FIG. 2, FIG. 3 and FIG. 4 the photonics crystal layer thus being. By way of comparison, a similar detector but without the photonics crystal layer is shown in FIG. 1, representing a detector according to prior art.

The photonics layer 120 corresponds with a nanostructured surface that diffracts the incident light resonantly into lateral guided modes. It is an advantage of embodiments according to the present invention that incident radiation from a particular wavelength can be coupled into a guided mode along the surface. If designed correctly, the guided mode can have an evanescent tail inside the medium, at the position of the fluorophores, with an optical intensity larger than that of the incident plane wave. This will result in an increased excitation of the fluorophores, and thus an increased fluorescence for the same incident light intensity. In addition, excitation of fluorophores in suspension above the sample, or excitation of fluorescent centers in the fluidic channel (auto fluorescence) is not enhanced. Hence this approach also suppresses any parasitic fluorescence that may occur in the measurement cell.

Embodiments of the present invention thus combine the following two advantages: (1) a large part of the incident radiation is now redirected in the lateral direction, away from the detector, which (2) results in an effective enhancement of the optical field at the surface of the sensor, which helps to reduce the total incidence power with the same number. Both effects result in an effective lowering of the optical power towards the detector and hence relax the requirements of the integrated filter.

In a second aspect, the present invention relates to a detection system for detecting fluorescence radiation. Such a detection system typically comprises a detector as described in the first aspect. The detection system furthermore typically may comprise an irradiation source for generating an excitation radiation beam for exciting the fluorescent particles to be characterized. Such an irradiation source typically may be a laser system, although embodiments are not limited thereto. The irradiation source typically may be selected such that it substantially does not emit in the wavelength region of the fluorescence radiation. Other components that typically may be present in a fluorescence detection system are known by the person skilled in the art. FIG. 4 illustrates a detection system 400 comprising an integrated fluorescence detector 100 as described above. The detection system 400 for example also comprises a controller 410 for controlling and timing operation of the radiation source 420 and the detector 112. The detection system 400 also may comprise read-out circuitry 430 for the detector 112. Other components, not indicated, may comprise additional optical components, sample holders, processors for processing read-out of the sensors, etc.

In a third aspect, the present invention relates to a method for detecting fluorescence radiation from fluorescent particles. The method comprises, according to embodiments of the present invention, providing an interaction between a sample comprising fluorescent particles and a sensing layer, providing an excitation radiation beam for exciting fluorescent particles accommodated on the sensing layer, and guiding excitation radiation away from a detection element by diffracting the excitation radiation in a lateral direction using a photonics crystal, the photonics crystal comprising absorption material such and being designed such that the photonics crystal layer is configured for diffracting incident excitation radiation into a lateral direction in which the photonics crystal layer (120) extends for incident excitation radiation having a wavelength in a wavelength range spanning at least 10 nm around the predetermined excitation wavelength. The advantage of performing the method as such is that it allows for both avoiding a substantial part of the excitation radiation to reach the detector and for increasing the photonic filed, as the excitation radiation is guided in the direction of the sample more than once such that the chance of exciting a fluorescent particle is increased, whereby environmental and process variations effecting the device do not significantly influence advantageous operation of the device.

By way of illustration, embodiments of the present invention not being limited thereto, an exemplary method is described below, illustrating standard and optional steps of a method according to a particular embodiment.

In a first step, the method comprises where necessary, providing fluorescent particles so as to label the target particles of interest with the fluorescent particles. In this way, by characterizing the fluorescent particles, characterization of the target particles indirectly is also obtained.

In a second step, the method comprises allowing interaction between a sensing layer adapted for accommodating the fluorescent particles and the sample, or more particularly the fluorescent particles. This may in one example be performed by guiding a fluid sample over the sensing layer, e.g., guiding the fluid sample in a microfluidic channel overlaying the sensing layer. The required timing for allowing interaction as well as the optimum conditions (e.g., temperature) may be selected as function of the application.

The method may optionally also comprise washing steps so as to clean the environment from unbounded fluorescent particles. On the other hand, the effect of fluorescence emitted by particles not close to the surface will be limited, especially as part of the excitation occurs in an evanescent tail of the optical mode.

After the fluorescence particles to be characterized are bound, the particles are excited using an excitation radiation beam guided to the sensing surface. Part of the excitation radiation will indeed induce fluorescence upon first interaction with the fluorescent particles. Nevertheless, part of the excitation radiation beam will not, and may enter the substrate. As there is a risk that the excitation radiation disturbs the detection of the fluorescence, according to embodiments of the present invention, it is avoided that the excitation radiation (or at least part, advantageously the biggest part) reaches the detection element.

Therefore, in a next step, the excitation radiation impinging on the substrate is diffracted in the substrate in a lateral direction, i.e. parallel to the substrate. The latter is obtained by letting the excitation radiation interact with a photonic crystal layer that is sensitive for interaction with radiation from the wavelength range of the excitation radiation. This step furthermore has the advantage that, if appropriate arrangement of the photonic crystal layer is provided, the diffracted excitation radiation will propagate in a mode having an evanescent tail overlapping the sensing layer. The latter may result in the fluorescent particles having a further interaction with the excitation radiation, thus increasing the chance of being excited and emitting fluorescent radiation. The photonic crystal layer thereby comprises absorption material such and being designed such that the photonics crystal layer is configured for diffracting incident excitation radiation into a lateral direction in which the photonics crystal layer extends for incident excitation radiation having a wavelength in a wavelength range spanning at least 10 nm around the predetermined excitation wavelength. The method furthermore comprises the steps of detecting the fluorescence radiation in a detection element, processing the obtained results and outputting the processed results.

By way of illustration, embodiments of the present invention not being limited thereto, particular examples will be discussed further below, the examples illustrating features and advantages of embodiments according to the present invention.

Figure 5:
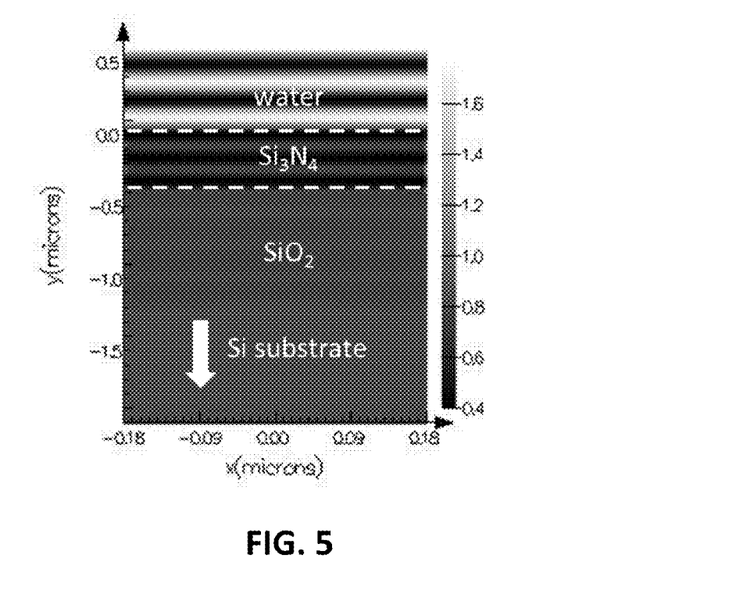
FIG. 5 illustrates the simulated optical intensity profile for radiation incident on a silicon substrate with a flat $Si_3N_4$ layer for comparison with a structure according to an embodiment of the present invention as shown in FIG. 6.
Figure 6:
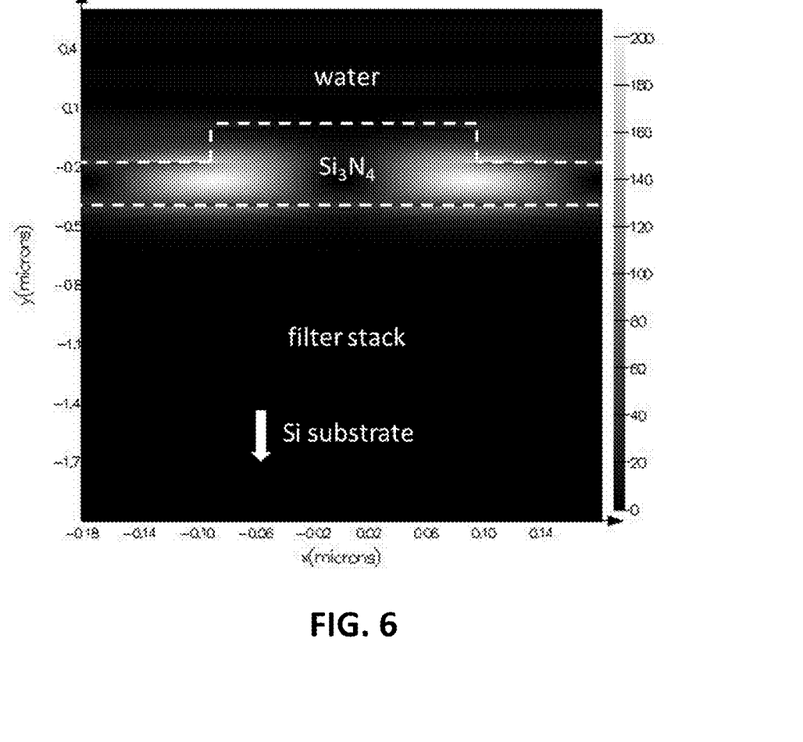
FIG. 6 illustrates the simulated optical intensity profile for radiation incident on a silicon substrate with a $Si_3N_4$ based periodic grating.

In a first example the optical intensity profiles for radiation incident on a Si substrate are shown in FIG. 5 and FIG. 6, for a system wherein a photonics crystal layer is used, but still without the presence of absorption material as used in embodiments of the present invention. In FIG. 5 the radiation passes through a flat $Si_3N_4$ layer (i.e. no photonic crystal layer is present) whereas in FIG. 6 a grating being a photonic crystal with variation in one direction, according to an embodiment of the present invention, is present on top of the Si substrate. In between the Si3N4 layer and the Si substrate a further rejection filter may be present. The grating in the first example is a simple periodic grating comprising a 400 nm thick Si3N4 waveguide etched down periodically to a depth of 178 nm. The period of the grating in this specific embodiment is 360 nm with a filling factor of 0.5 (e.g. in the exemplary embodiment the lines and trenches are 180 nm wide). FIG. 5 shows that a non-patterned surface results in a standing wave pattern caused by interference between the incident and reflected waves. The intensity profile of FIG. 6, where a pattern is realized through periodic etching, shows a strongly increased intensity not only inside the $Si_3N_4$ layer but also in selected areas above the surface inside the water film.

Figure 7:
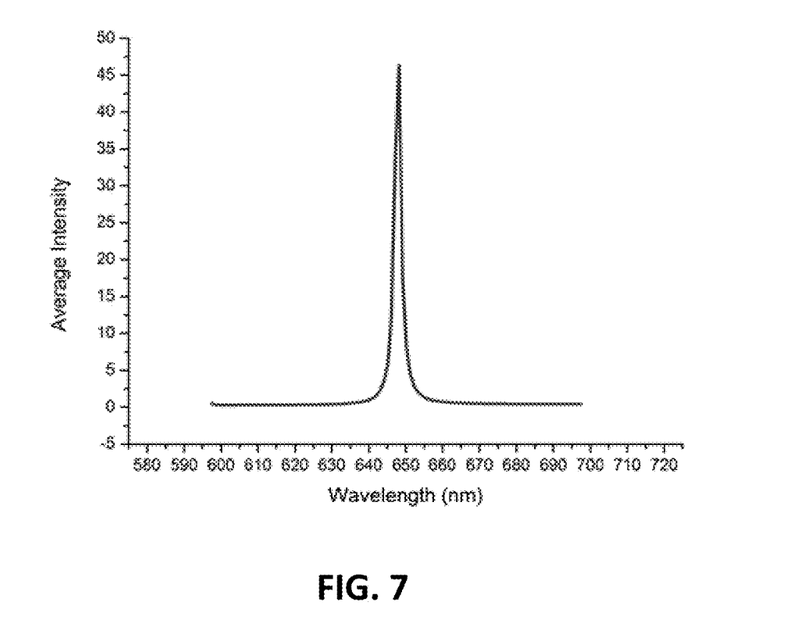
FIG. 7 illustrates the optical intensity at a height of 3 nm above the surface, averaged over the entire surface, illustrating an advantage according to an embodiment of the present invention.

FIG. 7 shows the average intensity at a height of 3 nm above the surface of the grating (i.e. the etched Si3N4 waveguide) of FIG. 6. As can be seen from FIG. 7 the averaged intensity is strongly wavelength dependent. The maximum intensity is close to 50, whereas the intensity without grating is only 0.7 (in the same arbitrary units). Therefore embodiments of the present invention enable a more efficient excitation of the fluorescent particles. In this first example an enhancement of the intensity with a factor 70 was even realized. This enhancement in intensity is not only visible in FIG. 7 but also in FIG. 5 and FIG. 6 showing a big difference in the intensity scales.

The resonance peak, shown in FIG. 7, is very sharp. It has a FWHM of 2.4 nm. The intensity enhancement drops by a factor of 2 for a 1.2 nm peak shift, and by a factor of 10 for a 3.3 nm peak shift. From simulations the following sensitivities to process and environmental variations are found for the resonance mode of a photonic crystal layer ($\Delta\lambda$res indicating the shift of the resonance wavelength):

etch depth: $\Delta\lambda$res/$\Delta$etch depth=0.27 nm/nm
refractive index of the surrounding medium: $\Delta\lambda$res/$\Delta$RI=36.8 nm/RIU
grating period: $\Delta\lambda$res/$\Delta$period=1.34 nm/nm
duty cycle: $\Delta\lambda$res/$\Delta$change in duty cycle=11.9 nm/DCU ("duty cycle unit": runs from 0 to 1).
Corresponding sensitivity to stripe width variations, for a period of 360 nm (1 DCU=360 nm): $\Delta\lambda$res/$\Delta$stripe width=0.033 nm/nm
sidewall angle of the waveguide of the photonics crystal layer: $\Delta\lambda$res/$\Delta$angle=0.41 nm/°

This means that the first example is sensitive for variations in the process and in the environment because of the small bandwidth of the resonance peak in FIG. 7. The maximum allowed variations for a factor 2 drop in intensity (1.2 nm peak shift) are rather strict:

etch depth: 4.5 nm
refractive index of the surrounding medium: 0.033 RIU
grating period: 0.9 nm
stripe width: 36.3 nm
sidewall angle: 2.9°

Figure 8:
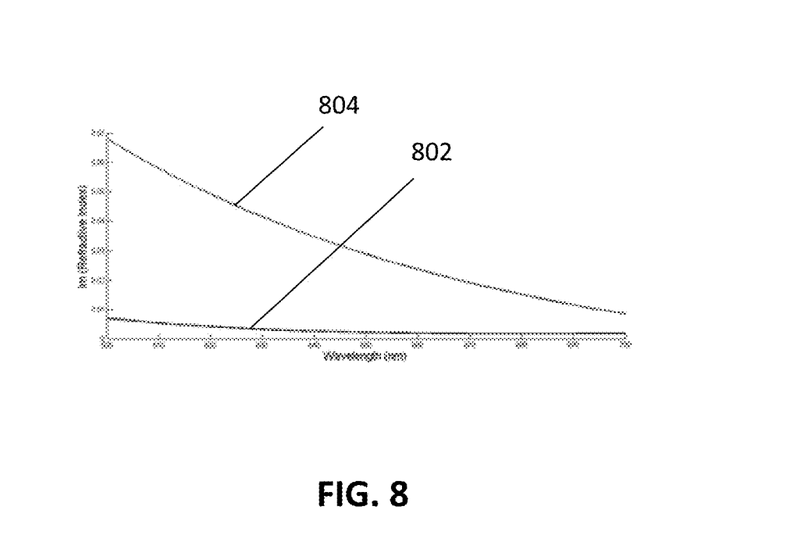
FIG. 8 illustrates the experimental loss factors for high-loss and low-loss materials used for modelling resonance in a sensor according to an embodiment of the present invention

To cope with the particular limitations indicated above, embodiments of the present invention make use of absorption material in the photonics crystal layer as illustrated in the second example. In the second particular example it is illustrated how the resonance peak can be broadened by for example adding damping. FIG. 8 shows experimental loss factors for a high-loss material and for a low-loss material in function of the wavelength. Curve 802 shows the experimental loss-factor for the low-loss material and curve 804 shows the experimental loss factor for the high-loss material.

Figure 9:
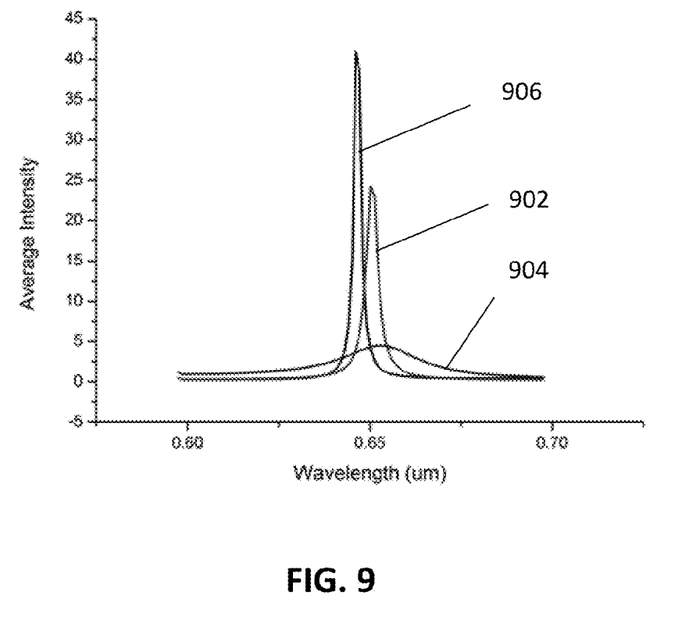
FIG. 9 illustrates the optical intensity at a height of 3 nm above the surface, averaged over the entire surface for high loss and low loss materials in comparison with loss-less material, illustrating features of an embodiment of the present invention.

These parameters are used in the following simulations. FIG. 9 shows the optical intensity at a height of 3 nm above the surface of the grating averaged over the entire surface. Curve 906 shows the optical intensity for a no-loss material. Curve 902 shows the optical intensity for a low-loss material. Curve 904 shows the optical intensity for a high loss material.

It can be seen from the simulations in FIG. 9 that the resonance peak is broadened when going from low loss to high loss material.

Figure 10:
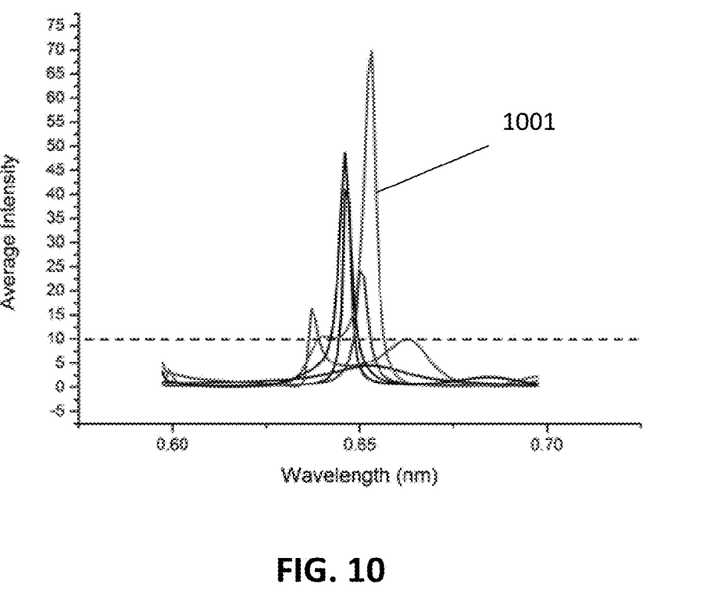
FIG. 10 illustrates the optical intensity for various optimized materials and rejection filters, as can be obtained using embodiments of the present invention.

FIG. 10 illustrates the optical intensity in various scenarios of joint optimization of the grating with the rejection filter. The dotted horizontal line indicates an average intensity of 10. Joint optimization of the grating with the rejection filter helps to achieve a wide wavelength range (e.g. curve 1001 in FIG. 10). This makes the enhancement insensitive to processing and environmental variations.

The above examples show the following particular optical characteristics:

The grating reduces the transmission of the incident light. The grating therefore takes over part of the function of the rejection filter. The requirements of the rejection filter may thus be relaxed (e.g. the optical density, hence the number of layers).

Figure 11:
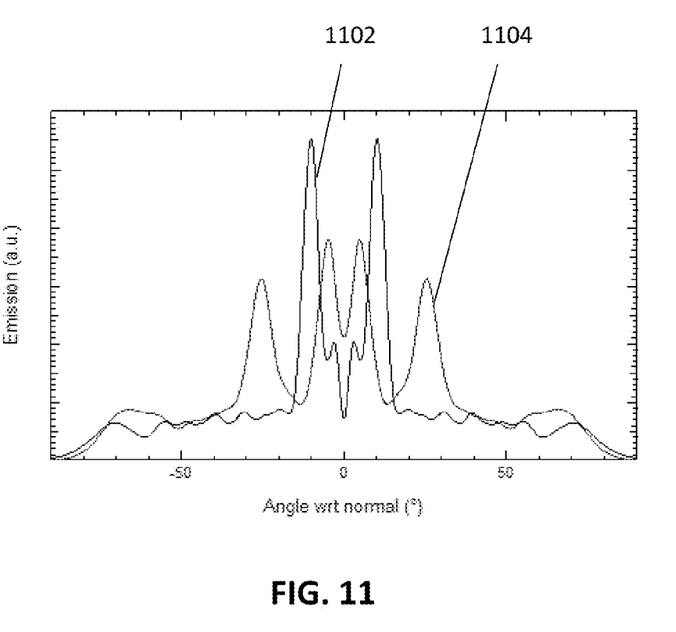
FIG. 11 illustrates a 2 dimensional emission profile for a fluorophore layer 3 nm above the surface, as can be obtained in embodiments according to the present invention.

The grating modifies the emission profile of the fluorophores. The emission is no longer isotropic but has lobes depending on the direction the light. This is illustrated in FIG. 11 showing the emission intensity in function of the angle for an exemplary embodiment where a fluorophore layer is present 3 nm above the surface of the grating. The angle in the graph of FIG. 11 is the angle of the light with the normal to the surface of the grating. Both are oriented in the direction of the substrate. Curve 1102 shows the emission intensity in function of the angle for a low-loss grating material. Curve 1104 shows the emission in function of the angle for a high-loss grating material. Since the emission profile of the fluorophores is modified, this may influence the transmission of the fluorescence through the rejection filter.

Figure 12:
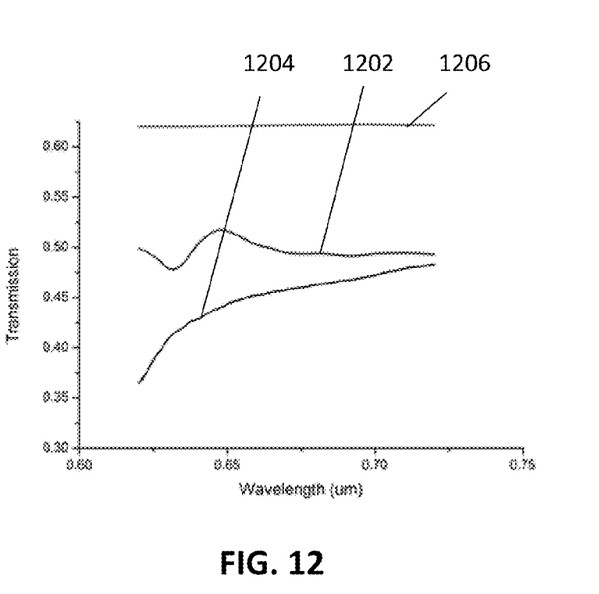
FIG. 12 illustrates the transmission to the substrate as function of the wavelength of the fluorescence emitted by a fluorophore layer 3 nm above the surface in a system comprising gratings according to embodiments of the present invention in comparison to a system without grating.

FIG. 12 illustrates the transmission of the fluorescent light to the substrate in function of the wavelength. This is illustrated for the case when no grating is present (curve 1106), for the case when a grating made of low-loss material is present (curve 1202), and for the case when a grating made of high-loss material is present (curve 1204). Without grating, slightly more than half of the emitted light (64%) is emitted towards the Si substrate, less than half (36%) is emitted away from the substrate (Purcell effect, because of the higher refractive index of Si, the optical density of states is higher than in the surrounding medium, enhancing light emission towards the substrate). If a lossy material is used, part of the fluorescent light will also be absorbed and not reach the Si substrate. With a low-loss grating, about 50% of the fluorescent light reaches the substrate, the remainder is either radiated away from the substrate or absorbed in the grating (curve 1202). With a high-loss grating, the loss is more severe at short wavelength (curve 1204). Curve 1204 also shows that at the emission peak of ATTO 647N (a fluorescent label with a wavelength of 670 nm), still about 45% of the fluorescence reaches the substrate.

The higher the loss of the grating material the more the excitation light will be absorbed. The absorption of the excitation light will also lead to the heating of the carriers. Therefore the absorption and heating is one of the parameters which needs to be taken into account when designing and optimizing embodiments of the present invention. Other coupled parameters which need to be taken into account simultaneously are (non-exhaustive list): the reduced incident laser power, the transmission of the grating and the reflection filter at the fluorescence wavelengths, the performance of the sense amplifier, the thermal design and actual cooling power of the system.

What is claimed is:

1. An integrated fluorescence detector for detecting fluorescent particles comprising:
    a substrate comprising an integrated detection element for detecting fluorescent radiation from fluorescent particles upon excitation of the fluorescent particles with incident excitation radiation;
    a sensing layer adapted for accommodating fluorescent particles to be sensed; and
    a photonics crystal layer arranged between the sensing layer and the substrate, the photonics crystal layer comprising an absorption material arranged such that the photonics crystal layer diffracts, into a lateral direction in which the photonics crystal layer extends, incident excitation radiation having a wavelength within at least 10 nm of a predetermined excitation wavelength.

2. The integrated fluorescence detector of claim 1, wherein the integrated fluorescence detector is configured for use with a predetermined fluorescent dye, and wherein the absorption material has an extinction coefficient in a range between 0.03 and 0.3 in a wavelength range in which the fluorescent dye absorbs the incident excitation radiation and an extinction coefficient below 0.03 in a wavelength range in which the fluorescent dye emits the fluorescent radiation.

3. The integrated fluorescence detector of claim 1, wherein the photonics crystal layer is arranged with respect to the sensing layer such that, upon propagation of the diffracted incident excitation radiation into the lateral direction in which the photonic crystal layer extends, a propagation mode of the diffracted incident excitation radiation has an evanescent tail in the sensing layer that allows for further excitation of the fluorescent particles accommodated at the sensing layer.

4. The integrated fluorescence detector of claim 1, wherein the photonics crystal layer comprises a waveguide and a grating.

5. The integrated fluorescence detector according to claim 4, wherein the grating is a structure that varies in one dimension.

6. The integrated fluorescence detector of claim 1, wherein the photonics crystal layer comprises a grating with a structure that varies in two dimensions.

7. The integrated fluorescence detector of claim 1, wherein the sensing layer is functionalized for binding the fluorescent particles.

8. The integrated fluorescence detector of claim 1, wherein the photonics crystal layer is made of a complimentary-metal-oxide-semiconductor-processable material.

9. The integrated fluorescence detector of claim 1, further comprising a microfluidic channel arranged either on or over the sensing layer and configured to allow a sample to be characterized to interact with the sensing layer.

10. The integrated fluorescence detector of claim 1, wherein the integrated fluorescence detector is an integrated optical detector embedded in the substrate.

11. A fluorescence detection system comprising an integrated fluorescence detector for detecting fluorescent particles using incident excitation radiation having a predetermined excitation wavelength, the integrated fluorescence detector comprising:
    a substrate comprising an integrated detection element for detecting fluorescent radiation from fluorescent particles upon excitation of the fluorescent particles with the incident excitation radiation;
    a sensing layer adapted for accommodating fluorescent particles to be sensed; and
    a photonics crystal layer arranged between the sensing layer and the substrate, the photonics crystal layer comprising an absorption material arranged such that the photonics crystal layer diffracts, into a lateral direction in which the photonics crystal layer extends, incident excitation radiation having a wavelength within at least 10 nm of the predetermined excitation wavelength.

12. The fluorescence detection system of claim 11, further comprising an excitation source for generating the incident excitation radiation.

13. A method for detecting fluorescent radiation from fluorescent particles, the method comprising:
   providing an interaction between a sample comprising fluorescent particles and a sensing layer;
   providing an excitation radiation beam for exciting fluorescent particles accommodated on the sensing layer; and
   guiding the excitation radiation away from a detection element by diffracting the excitation radiation in a lateral direction using a photonics crystal, the photonics crystal comprising an absorption material arranged to cause the photonics crystal to diffract the incident excitation radiation into the lateral direction in which the photonics crystal extends when the incident excitation radiation has a wavelength within at least 10 nm of a predetermined excitation wavelength.

* * * * *